United States Patent [19]

Champseix et al.

[11] 4,433,150

[45] Feb. 21, 1984

[54] 2-(4-PIPERIDYL)-1-(4-QUINOLYL)-ETHA-NONES AND ETHANES

[75] Inventors: Alain A. Champseix, Orsay; Gerard R. Le Fur, Plessis Robinson; Christian L. A. Renault, Taverny, all of France

[73] Assignee: Pharmindustrie, Gennevilliers, France

[21] Appl. No.: 212,293

[22] Filed: Dec. 2, 1980

[30] Foreign Application Priority Data

Dec. 21, 1979 [FR] France ............... 79 31396

[51] Int. Cl.³ ............... C07D 401/06; A61K 31/47
[52] U.S. Cl. ............... 546/168; 546/176; 424/258
[58] Field of Search ............... 546/176, 171, 156, 168, 546/177

[56] References Cited

U.S. PATENT DOCUMENTS 2,492,487 12/1949 Koepfli et al. ............... 546/168

FOREIGN PATENT DOCUMENTS 2177511 9/1973 France .
2354771 1/1978 France .
31753 7/1981 France ............... 424/258
42781 12/1981 France ............... 546/177

Primary Examiner—Paul M. Coughlan, Jr.
Assistant Examiner—D. B. Springer
Attorney, Agent, or Firm—Beveridge, DeGrandi & Kline

[57] ABSTRACT

Compounds, useful as medicaments, of the formula:

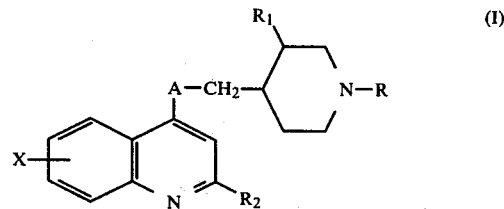

in which R is hydrogen, alkyl, alkenyl or arylalkyl, $R_1$ is hydrogen, alkyl or alkenyl, $R_2$ is hydrogen, alkyl, arylalkyl, phenyl, pyridyl, thienyl or substituted phenyl, X is hydrogen, halogen, alkyl, alkoxy, alkylthio, trifluoromethyl, nitro, amino or amino substituted by one or two alkyl groups, and A represents a CO or $CH_2$ group.

14 Claims, No Drawings

2-(4-PIPERIDYL)-1-(4-QUINOLYL)-ETHANONES AND ETHANES

The present invention relates to new derivatives of 2-(4-piperidyl)-1-(4-quinolyl)-ethanone which may be used as medicaments or as intermediate products for the manufacture of medicaments.

Those derivatives may be represented by the general formula:

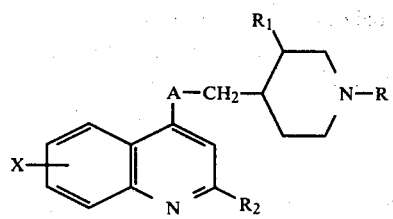

in which

R represents a hydrogen atom, an alkenyl group having 3 or 4 carbon atoms, an alkyl group containing 1 to 4 carbon atoms or an arylalkyl group, especially phenylalkyl, of which the alkyl part contains 1 or 2 carbon atoms;

$R_1$ represents a hydrogen atom, an alkyl group having 1 to 4 carbon atoms or an alkenyl group having 2 to 4 carbon atoms;

$R_2$ represents a hydrogen atom, an alkyl group having 1 to 4 carbon atoms, an arylalkyl group, especially phenylalkyl, of which the alkyl part contains 1 or 2 carbon atoms, a phenyl, pyridyl or thienyl group, or a phenyl group substituted by one or two substituents selected from the halogen atoms (chlorine, fluorine, bromine, iodine), the alkyl, alkoxy and alkylthio groups having 1 to 4 carbon atoms, the trifluoromethyl group, the nitro group and the amino group, the latter being possibly substituted by one or two alkyl groups having 1 or 2 carbon atoms;

X is fixed in position 5, 6, 7 or 8 on the quinoline ring and represents a hydrogen or halogen (chlorine, fluorine, bromine, iodine) atom, an alkyl, alkoxy or alkylthio group having 1 to 4 carbon atoms, a trifluoromethyl group, a nitro group or an amino group, the latter being possibly substituted by one or two alkyl groups having 1 to 2 carbon atoms; and A represents a CO or a CH2 group.

In the formula (I) above, $R_2$ is preferably a phenyl or substituted phenyl group.

When $R_1$ is not a hydrogen atom, the molecule of the compounds of formula (I) contains two asymmetric carbon atoms and therefore, for a given meaning of R, $R_1$, $R_2$, A and X, there are two diastereoisomers named, respectively, a cis and a trans compound according as the group $R_1$ and the group fixed in position 4 on the piperidine ring are in the cis or trans position with respect to one another. These two diastereoisomers may be represented diagrammatically by the formulae ($I_a$) and ($I_b$) below:

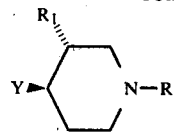

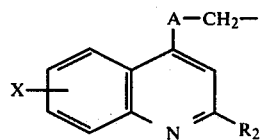

in which formulae Y represents the group:

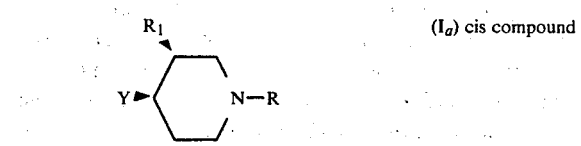

To each diastereoisomer correspond a racemic form and two enantiomers, each enantiomer corresponding to a determined absolute configuration of the carbon atoms in positions 3 and 4 of the piperidine ring.

The various isomers indicated above are part of the invention, as well as the salts of addition of the compounds corresponding to the planar formula (I) with mineral or organic acids. The acids form pharmaceutically acceptable salts. Examples of such acids are hydrochloric, hydrobromic, sulfuric, nitric, acetic, propionic, tartaric, citric, methanesulfonic, fumaric, maleic and succinic acids.

The compounds of general formula (I) for which A represents the CH2 may be prepared by reduction of the corresponding products of the general formula (I) for which A represents the CO group, according to the following reaction scheme:

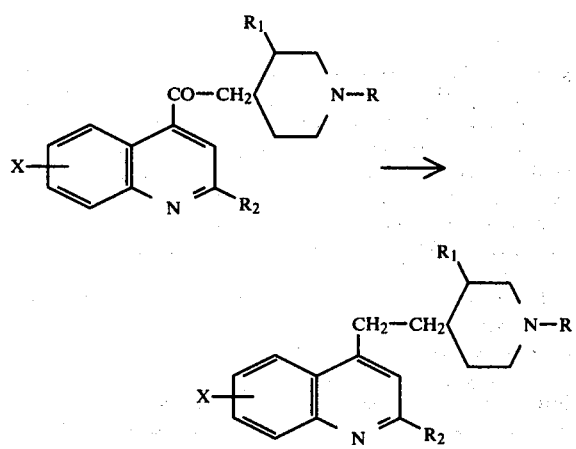

Methods known in the art which allow a CO group to be converted into a CH2 group are used for this reduction, for example, those described by R. B. WAGNER and H. D. ZOOK (Synthetic Organic Chemistry, p.5, J. WILEY and Sons-1953), relied on herein. The reducing agent used is advantageously hydrazine hydrate in the presence of an alkali metal hydroxide such as sodium or potassium hydroxide, in an inert solvent such as an alcohol or a diol, for example, diethyleneglycol, at a temperature between 100° C. and 180° C.

The products of general formula (I) for which A represents the CO group and R a hydrogen atom may be prepared by condensation of an ester of quinoline-4-carboxylic acid of formula (II) with an ester of 4-piperidine-acetic acid of formula (III), then hydrolysis and decarboxylation of the compound of formula (IV) thus obtained, according to the following reaction scheme:

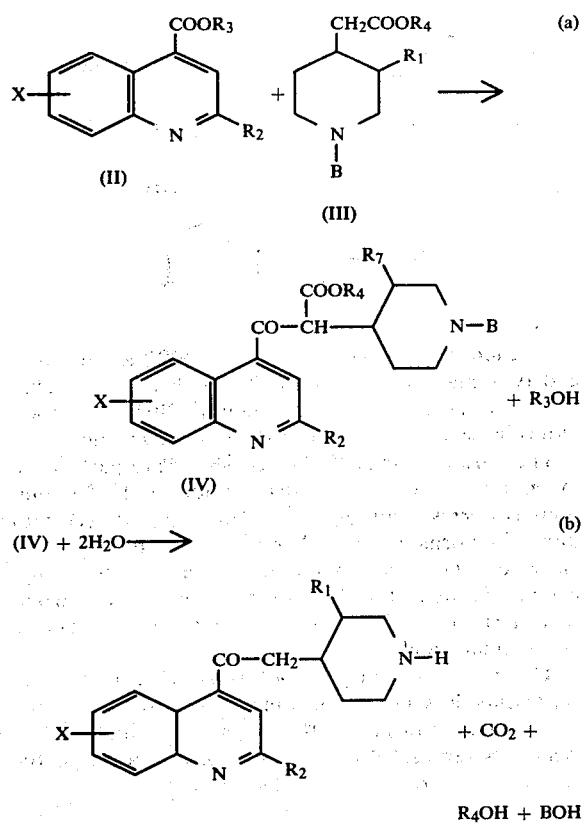

In the above formulae $R_3$ and $R_4$ represent alkyl groups of low molecular weight, for example methyl or ethyl, and B represents a group which protects the amine function and which is stable in anhydrous alkaline medium and can be eliminated in acid medium, such as those which are described by R. A. BOISSONNAS, Advances in Organic Chemistry 3, page 159, Interscience (1963). Advantageously the benzoyl group (—B═—CO—C$_6$H$_5$) or the benzyloxycarbonyl group (—B═—CO—O—CH$_2$—C$_6$H$_5$) is used.

In order to carry out the condensation reaction (a) processes known in the prior art are called for (cf. "The acetoacetic acid ester condensation", C. R. HAUSER et al., Organic Reactions, Vol. 1, p. 266, WILEY and Sons, 1942). The operation is advantageously effected in the presence of a base such as an alcoholate (for example, potassium tertiobutylate) or a metal hydride (for example sodium or potassium hydride), in an inert solvent such as a hydrocarbon or another aprotic solvent (for example, tetrahydrofuran), at a temperature between 0° C. and the boiling temperature of the solvent used.

The hydrolysis reaction (b) is effected by processes known in the art (cf. "Cleavage of β-keto-esters", R. B. WAGNER and H. D. ZOOK, Synthetic Organic Chemistry, p. 237, WILEY and Sons, 1953). The most usual method consists in heating with boiling the product of formula (IV) in an aqueous solution of an acid such as hydrochloric or sulphuric acid.

The starting substances of formula (II) are easily accessible by the methods described in the literature (cf. Quinolines-Heterocyclic compounds-32, 274, WILEY and Sons, 1977). The same applies to the compounds of formula (III) (cf. W. E. DOERING and J. D. CHANCEY, J. Am. Chem. Soc. 1946, 68, 586; V. PRELOG, Helv. Chim. Acta, 1944, 37, 535; R. F. BORNE, J. Heterocycl, Chem. 1972, 9, 869).

The compounds of general formula (I) for which R is an alkyl, alkenyl or arylalkyl group may be prepared by the action of an alkylating agent on the corresponding compounds of formula (I) for which R is a hydrogen atom. As alkylating agents may be particularly mentioned the halides of formula R-Hal, the sulphates of formula (R)$_2$SO$_4$ and the alkyl or arylsulphonates of formula ArSO$_3$R or R'SO$_3$R, formulae in which R represents an alkyl group having 1 to 4 carbon atoms, an alkenyl group having 3 or 4 carbon atoms or an arylalkyl group of which the alkyl part has 1 or 2 carbon atoms, Ar represents an aryl group and R' represents an alkyl group. The reaction may be shown diagrammatically as follows in the case where a halide is used as alkylating agent:

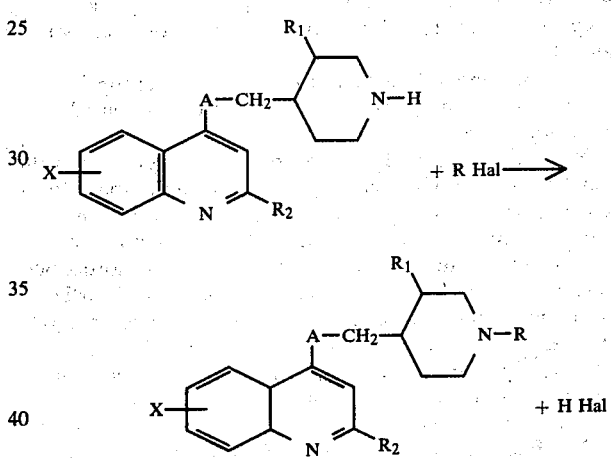

The alkylation reaction of the compounds of formula (I) for which R═H by means of an alkylating agent is effected according to processes known in the art, such as those described by R. B. WAGNER and H. D. ZOOK (Synthetic Organic Chemistry, p. 666, J. WILEY and Sons, 1965). The operation is advantageously effected in the presence of an organic or mineral base (for example sodium or potassium carbonate), in an inert solvent, for example dimethylformamide.

A variant for the preparation of the products of general formula (I) for which A represents the group CH$_2$ and R represents an alkyl or arylalkyl group consists in reacting the corresponding products of formula (I) for which A represents the group CH$_2$ and R represents a hydrogen atom with an acid chloride or a chloroformic ester of formula Z—CO—Cl, in which Z represents an alkyl group having 1 to 3 carbon atoms, an aryl group, an arylalkyl group of which the alkyl part has one carbon atom or a low alkoxy group (for example methoxy or ethoxy), and then reducing by means of a hydride the compound of formula (V) thus obtained, according to the reaction scheme which follows:

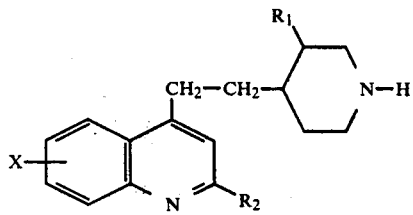

(c)

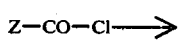

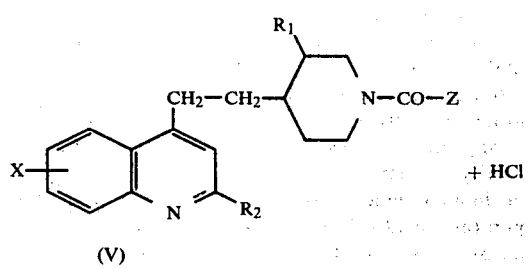

(V)

(V) $\xrightarrow{\text{reducing hydride}}$ (d)

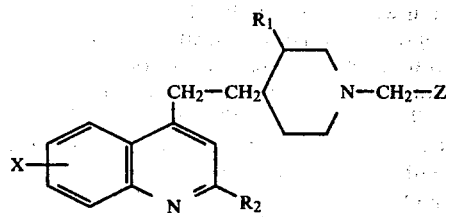

(V) $\xrightarrow{\text{reducing hydride}}$ (d) bis

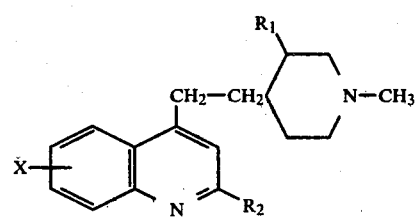

The reaction (d) corresponds to the case where Z is alkyl, aryl or arylalkyl, and the reaction (d) bis to the case where Z is lower alkoxy.

To carry out the reaction (c), methods known in the art are used which enable a secondary amine to be converted into an amide (case Z=alkyl, aryl or aralkyl) or into a carbamate (case Z=alkoxy), for example those described by R. G. WAGNER and H. D. ZOOK (Synthetic Organic Chemistry, p. 565 and p. 646, J. WILEY and Sons, 1953). The operation is generally effected in the presence of a base such as sodium hydroxide in aqueous solution or triethylamine, in an inert solvent such as chloroform or 1,1,1-trichloroethane, at a temperature between 0° C. and 30° C.

The reactions (d) and (d) bis, also use known methods (cf. for example, R. B. WAGNER and H. D. ZOOK, Synthetic Organic Chemistry, p. 660, J. WILEY and Sons, 1953). As the reducing hydride is advantageously used lithium aluminum hydride or other complex hydrides such as the hydride of sodium and bis (2-methoxy-ethoxy) aluminum, in an inert solvent such as an ether or an aromatic hydrocarbon.

The products of formula (I) for which A represents the group $CH_2$, R represents a hydrogen atom and $R_2$ does not represent a hydrogen atom can also be prepared from corresponding products of formula (I) for which $R_2$ represents a hydrogen atom according to the following reaction scheme in four stages:

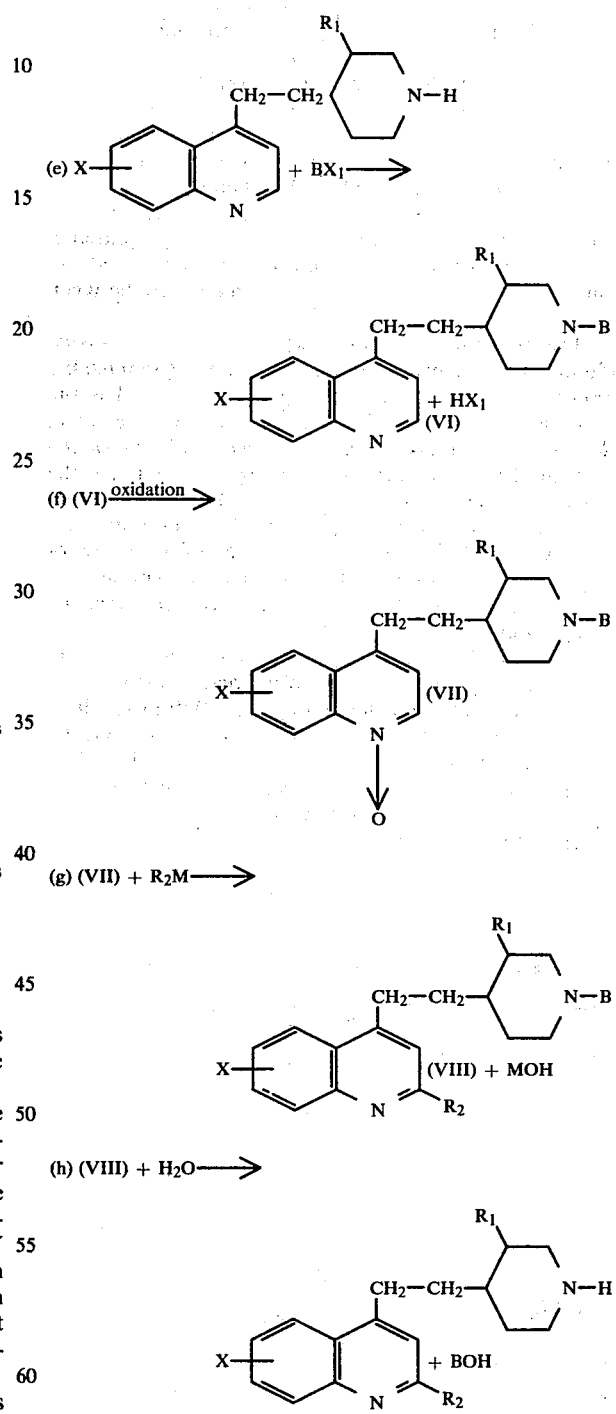

The reaction (e), which aims to protect the piperidine amine function, consists in reacting a compound of formula (I) in which A is $CH_2$ and R and $R_2$ are hydrogen atoms with a compound $BX_1$ which allows the replacement of the hydrogen atom fixed on the nitrogen of the piperidine ring by a protecting group B, stable in the presence of organometallic compounds and capable of being eliminated in acid medium. The protecting groups generally used are acyl groups described by R. A. BOISSONNAS (Advances in Organic Chemistry, 3, p. 159, Interscience, 1963), for example, the benzoyl group. As the compound $BX_1$ permitting the above replacement may be mentioned the acyl halides, especially benzoyl chloride. The reaction (e) is then carried out under the conditions analogous to those used for reaction (c).

To carry out the oxidation reaction (f), the methods known in the art are used which enable the nitrogenous heterocycles to be oxidized on the nitrogen (cf. for example, A. R. KATRITZKY et al., Chemistry of the Heterocyclic N-oxides, Organic Chemistry, 19, p. 21, Academic Press, 1971). As oxidizing agent are advantageously used peroxides such as monoperphthalic, paranitroperbenzoic or metachloroperbenzoic acids, in an inert solvent such as ether, at a temperature between 0° C. and 25° C.

The reaction (g) consists in reacting the N-oxide obtained in the previous stage with an organometallic compound of the formula $R_2M$, in which $R_2$ has the same significance as in formula (I) except hydrogen and M represents an alkali metal, especially lithium, or the radical MgHal, Hal denoting a halogen atom, under the conditions described by A. R. KATRITZKY et al. (same reference as above, p. 308). The operation is advantageously effected in the presence of an excess of organometallic compound, in an inert solvent such as other, tetrahydrofuran or an aromatic hydrocarbon, at a temperature from 0° C. to 25° C.

The hydrolysis reaction (h) is effected under the conditions analogous to those used for reaction (b).

The products of general formula (I) for which A represents the group $CH_2$, R is a hydrogen atom and $R_1$ is a hydrogen atom or an alkyl group with 1 to 4 carbon atoms, can also be prepared by reaction of monochlorocarbene: CHCl on the indole derivatives of formula (IX), according to the following reaction scheme:

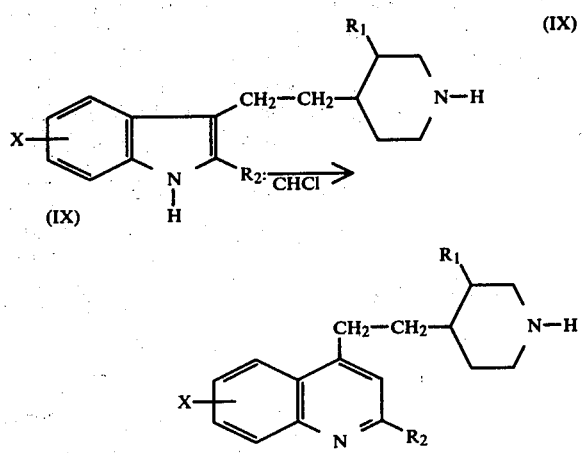

In the formula (IX) above $R_1$ is a hydrogen atom or an alkyl group having 1 to 4 carbon atoms and X and $R_2$ have the same significance as in formula (I).

The monochlorocarbene is prepared "in situ" by the action of a base on dichloromethane, according to known methods (cf. for example, H. DOBBS, Chem. Comm. 1965, 56 and J. Org. Chem. 1968, 33, 1093; CLOSS, J. Org. Chem. 1961, 26, 2609 and Tetrah. Letters 1976, 3179). Methyllithium is advantageously used as base, in an inert solvent such as ether or tetrahydrofuran, at a temperature between −30° C. and +20° C.

Indole derivatives of formula (IX) can be prepared according to known processes (cf. for example French Patent No. 2,334,358, B. P. No. 1,023,781 and J. Org. Chem. 1961, 26, 3368-3371.)

The compounds of general formula (I) for which R is a hydrogen atom and $R_1$ is an ethenyl (vinyl) group and for which the carbon atom of the piperidine ring carrying the vinyl group $R_1$ has a given configuration, rectus (R) or sinister (S), can be prepared by heating at a temperature greater than 50° C., in a protic solvent or a mixture of protic solvents, in the presence or absence of formaldehyde, the corresponding compounds of formula (I) for which R is a hydrogen atom and $R_1$ is a vinyl group and for which the carbon atom of the piperidine ring carrying the vinyl group $R_1$ has the inverse configuration, sinister (S) or rectus (R), partially or totally salified. The heating may be effected in particular in an aqueous acid medium of pH about 6, at a temperature of 120° C. to 160° C. This heating brings about an isomerisation of the starting substances.

The reaction mixtures obtained by the various processes previously described are treated according to conventional methods, physical (evaporation, extraction with a solvent, distillation, crystallization, chromatography, etc) or chemical (formation of salt and regeneration of the base, etc.) in order to isolate the compounds of formula (I) in a pure state.

The compounds of formula (I) in the form of the free base may if desired be converted into salts of addition with a mineral or organic acid by the action of such an acid in an appropriate solvent. Examples of suitable solvents are alcohols such as methanol, ethanol and isopropanol, ketones such as acetone and methyl ethyl ketone, diethyl oxide, and mixtures thereof.

The medicaments of the class of benzodiazepines are used as anticonvulsivants, as hypnotics and for the treatment of states of anxiety and of various psychoneurotic states for treatment of warm blooded mammals. The presence of specific receptors of the benzodiazepines in the membranes of the rat's brain has been shown [SQUIRES et al., Nature, 266, (1977), 732] and the degree of affinity of the benzodiazepines for these receptors, which is measured by their aptitude for displacing the tritiated Diazepam from its binding sites, is in good correlation with the pharmacodynamic effects observed on the animal and on man.

Until now, apart from the benzodiazepines, no medicament acting on the central nervous system has shown itself capable of displacing significantly the Diazepam from its binding sites [cf. BRAESTRUP et al., Europ. J. Pharmacol. 48, (1978) 26].

The products of the invention, although they have a structure different from those of the benzodiazepines, displace the Diazepam from its binding sites. They may therefore find applications as hypnotics, anticonvulsivants, and in the treatment of states of tension and anxiety resulting from stressful circumstances, or of somatic troubles linked to emotional factors. They may be used for the treatment of the psychoneurotic states manifested by symptoms of anxiety, apprehension, fatigue, agitation or depression.

The products of the invention also posses antiarhythmic properties.

The following examples illustrate the invention without it being limited thereto. The data relative to the nuclear magnetic resonance spectra (briefly: N.M.R. spectra) appearing in these examples relate to the nuclear magnetic resonance of the protons of the compounds in the form of a base. In order to effect the measures of nuclear magnetic resonance the compounds are dissolved in deuteriated chloroform.

EXAMPLE 1

2-(4-piperidyl)-1(4-quinolyl)-ethanone 14 ml of a 50% suspension of potassium hydride in oil are added under nitrogen to 11.5 g of ethyl quinoline-4-carboxylate in 100 ml of dry tetrahydrofuran. The mixture is brought to gentle ebullition, then a solution of 17.5 g of ethyl (N-benzyloxycarbonyl-4-piperidine)-acetate in 50 ml of dry tetrahydrofuran is added drop by drop, and the mixture is heated under reflux for 3 hours.

After cooling, 5 ml of ethanol are added, the solvent is removed by distillation under reduced pressure, the residue is taken up by 400 ml of a 5 N aqueous solution of hydrochloric acid and refluxed for 18 hours. The aqueous solution is washed twice with 100 ml of ether, then the pH is brought to 11 by addition of sodium hydroxide and the insoluble material is extracted twice by 100 ml of chloroform. The organic solution is washed with water and dried over magnesium sulphate. After elimination of the solvent by distillation under reduced pressure, 13 g of 2-(4-piperidyl)-1-(4-quinolyl)-ethanone are obtained in the form of an oil.

N.M.R. spectrum of the product obtained:
The chemical displacements δ of the protons are as follows:

| aromatics | δ: 7.6–9 ppm |
|---|---|
| $CH_2$—CO— | δ: 3 ppm |
| $CH_2$—N— | δ: 2.6–3.2 ppm |

EXAMPLE 2

1-(6-Methoxy-4-Quinolyl)-2-(4-Piperidyl)-Ethanone 10.6 g of ethyl (6-methoxy-quinoline)-4-carboxylate are added to 16.8 g of potassium t-butylate in 100 ml of dry tetrahydrofuran, then, drop by drop, a solution of 15 g of ethyl (N-benzyloxycarbonyl 4-piperidine)-acetate in 150 ml of dry tetrahydrofuran is added.

Stirring is effected for 18 hours at the ambient temperature, then the solvent is eliminated by distillation under reduced pressure and the residue is taken up by 300 ml of a 5 N aqueous solution of hydrochloric acid. The aqueous solution is refluxed for 4 hours, then washed with 100 ml of solution is refluxed for 4 hours, then washed with 100 ml of ether twice, made alkaline by addition of sodium hydroxide and extracted 3 times by 200 ml of methylene chloride. The organic solution is washed with water, dried and evaporated under reduced pressure. The crude base obtained is converted into hydrochloride by the action of hydrochloric acid in ethanol. 4 g of 1-(6-methoxy-4-quinolyl)-2-(4-piperidyl)ethanone are obtained in the form of monohydrated dihydrochloride, which melts at 160° C.

N.M.R. spectrum of the product obtained:

| aromatics | δ: 7.4–8.6 ppm |
|---|---|
| $CH_3O$ | δ: 3.9 ppm |
| $CH_2$—CO | δ: 2.9 ppm |
| —$CH_2$—N | δ: 2.6–3 ppm |

EXAMPLE 3

2-[3(R)-Ethenyl-4(S)-Piperidyl]-1-(6-Methoxy-4-Quinolyl)-Ethanone

A solution of 34 g of ethyl (6-methoxy-quinoline)-4-carboxylate in 300 ml of dry tetrahydrofuran is added at 0° C. to 51 g of potassium t-butylate in 200 ml of dry tetrahydrofuran, then a solution of 52 g of ethyl [1-benzoyl-3(R)-ethenyl-4(S)-piperidyl]-acetate in 300 ml of dry tetrahydrofuran is added. The mixture is stirred for 30 hours at the ambient temperature, then brought to dryness and the residue is taken up in 600 ml of water. The aqueous solution is washed with ether, neutralized with acetic acid and extract 4 times with 200 ml of methylene chloride. After evaporation of the solvent, 70 g of product are obtained. This product is heated under reflux for 9 hours in 600 ml of a 5 N aqueous solution of hydrochloric acid. Then the aqueous solution is made alkaline and the insoluble matter is extracted 4 times with 200 ml of methylene chloride. After evaporation of the solvent, 31 g of the desired product are obtained in the form of the base, which is converted into hydrochloride by the action of hydrochloric acid in acetone. After recrystallization from ethanol, 10.8 g of 2-[3(R)-ethenyl-4(S)-piperidyl]-1-(6-methoxy-4-quinolyl)ethanone are obtained in the form of the dihydrochloride, which melts at 200° C.

N.M.R. spectrum of the product obtained:

| aromatics | δ: 7.3–8.6 ppm |
|---|---|
| $CH_3O$ | δ: 3.9 ppm |
| C(H)=$CH_2$ | δ: 6 ppm |
| —CH=$CH_2$ | δ: 5 ppm |

EXAMPLE 4

2-(3-Methyl-4-Piperidyl)-1-(6-Methoxy-4-Quinolyl)Ethanone (Trans Isomer, Racemic)

The operation is as in Example 1, starting from 12.1 g of ethyl (6-methoxy-quinoline)-4-carboxylate, 34 ml of a 20% suspension of potassium hydride in oil, and 9.4 g of ethyl (1-benzoyl-3-methyl-4-piperidyl)-acetate (trans isomer). 3.7 g of 2-(3-methyl-4-piperidyl)-1-(6-methoxy-4-quinolyl)ethanone (trans isomer) are obtained in the form of an oil.

N.M.R. spectrum of the product obtained:

| aromatics | δ: 7.2 to 8.8 ppm |
|---|---|
| $CH_3$—O | δ: 3.9 ppm |
| $CH_3$— | δ: 1 ppm |
| —C—$CH_2$— ‖ O | δ: 3.1 ppm |

EXAMPLE 5

1-(2-Phenyl-4-Quinolyl)-2-(4-Piperidyl)-Ethanone

A solution of 21.2 g of methyl (2-phenyl-quinoline)-4-carboxylate in 50 ml of dry tetrahydrofuran is rapidly added to a suspension of 27.5 g of potassium t-butylate in 215 ml of dry tetrahydrofuran, placed under an atmosphere of nitrogen and cooled to 0° C. The temperature being maintained at less than +10° C., a solution of 22.1 g of ethyl (1-benzoyl-4-piperidyl)-acetate in 80 ml of dry tetrahydrofuran is slowly added in a period of 2 hours. The reaction mixture is then stirred for 20 hours at the ambient temperature, then brought to dryness by evaporation of the solvent. The residue is heated under reflux for 18 hours in 650 ml of a 5 N aqueous solution of hydrochloric acid.

After cooling, the solution obtaned is filtered and the filtrate is extracted twice by 250 ml of ether. The residual aqueous solution is concentrated under reduced pressure. The residue obtained is extracted by 500 ml of hot methanol and the solution from extraction is filtered. The filtrate, after evaporation of the methanol, gives 13.8 g of dihydrochloride of 1-(2-phenyl-4-quinolyl)-2-(4-piperidyl)-ethanone melting at 259° C.

N.M.R. spectrum of the product obtained:

| aromatics | δ: 7.3–8.2 ppm |
| —CH$_2$N and CH$_2$CO | δ: 2.2–3.2 ppm |

EXAMPLE 6

1-[2-(4-Fluoro-Phenyl)-4-Quinolyl]-2-(4-Piperidyl)Ethanone 12 g of sodium hydride in the form of a 50% suspension in vaseline oil are slowly added, incrementally, to 250 ml of dry tetrahydrofuran, under an atmosphere of nitrogen. The temperature being maintained at about 20° C., a solution of 15 g of ethyl (1-benzoyl-4-piperidyl)-acetate and 16 g of ethyl [2-(4-fluoro-phenyl)-quinoline]-4-carboxylate in 250 ml of dry tetrahydrofuran is rapidly introduced. The suspension obtained is left for 15 hours at the ambient temperature then heated for 6 hours under reflux. The reaction mixture is evaporated to dryness, the residue is taken up by 100 ml of methylene chloride and the mixture is again brought to dryness. To the residue obtained are added very slowly 300 ml of a 11 N aqueous solution of hydrochloric acid and the final mixture is heated for 15 hours under reflux. The aqueous solution obtained is extracted twice with 500 ml of ether. The residual aqueous solution is made alkaline by means of a 11 N aqueous solution of sodium hydroxide, then extracted twice with 300 ml each time of methylene chloride. After evaporation of the methylene chloride, are obtained 17.8 g of 1-[2-(4-fluoro-phenyl)-4-quinolyl]-2-(4-piperidyl)-ethanone, the fumarate of which, formed by the action of the fumaric acid in the ethanol, melts at 206° C.

N.M.R. spectrum of the product obtained:

| aromatics | δ: 7–8.4 ppm |
| CH$_2$N and COCH$_2$ | δ: 2.4–3.4 ppm |
| CH$_2$—(CH) | δ: 1–2.2 ppm |

EXAMPLE 7

1-[2-(4-Chloro-Phenyl)-4-Quinolyl]-2-(4-Piperidyl)-Ethanone

The operation is as in Example 6, but starting from 22 g of sodium hydride (50% suspension in oil), 29.7 g of methyl [2-(4-chloro-phenyl)-quinoline]-4-carboxylate and 26.1 g of methyl (1-benzoyl-4-piperidyl)-acetate. 22.2 g of 1-[2-2(4-chloro-phenyl)-4-quinolyl]-2-(4-piperidyl)-ethanone are finally obtained, the monomethane sulphonate of which, formed by the action of methanesulphonic acid in the ethanol, melts at 170° C.

N.M.R. spectrum of the product obtained:

| aromatics | δ: 7.2–8.4 ppm |
| CH$_2$N and COCH$_2$ | δ: 2.3–3.4 ppm |
| CH$_2$—(CH) | δ: 1–2.2 ppm |

EXAMPLE 8

1-[2-(4-Methyl-Phenyl)-4-Quinolyl]-2p-(4-Piperidyl)-Ethanone

The operation as in Example 2, but starting from 16.8 g of potassium t-butylate, 13.7 g of ethyl (1-benzoyl-4-piperidyl)-acetate and 14.5 g of ethyl [2-(4-methyl-phenyl)-quinoline]-4-carboxylate. 15.2 g of 1-[2p-(4-methylphenyl)-4-quinolyl]-2-(4-piperidyl) ethanone are obtained, the dihydrochloride of which melts above 260° C.

N.M.R. spectrum of the product obtained:

| aromatics | δ: 7.2–8.4 ppm |
| CH$_2$N and CH$_2$CO | δ: 2.2–3.2 ppm |
| CH$_3$Ar | δ: 2.4 ppm |

EXAMPLE 9

1-[2-(4-Methoxy-Phenyl)-4-Quinolyl]-2-(4-Piperidyl)Ethanone

The operation is as in Example 2, but starting from 28.5 g of potassium t-butylate, 25 g of methyl [2-(4-methoxy-phenyl)-quinoline]-4-carboxylate and 22.2 g of methyl (1-benzoyl-4-piperidyl)-acetate.

21.6 g of 1-[2-(4-methoxy-phenyl)-4-quinolyl]-2-(4-piperidyl) ethanone are obtained, the dihydrochloride of which melts above 260° C.

N.M.R. spectrum of the product obtained:

| aromatics | δ: 6.9–8.4 ppm |
| CH$_2$N and COCH$_2$ | δ: 2.4–3.4 ppm |
| CH$_3$O | δ: 3.8 ppm |

EXAMPLE 10

1-(7-Chloro-2-Phenyl-4-Quinolyl)-2-(4-Piperidyl)-Ethanone

The operation is as in Example 6, but starting from 24 g of sodium hydride (50% suspension in oil), 26.1 g of ethyl (1-benzoyl-4-piperidyl)-acetate and 31.1 g of ethyl (7-chloro-2-phenyl-4-quinolyl)-4-carboxylate. 28.5 g of 1-(7-chloro-2-phenyl-4-quinolyl)-2-(4-piperidyl) ethanone are obtained, the monomethanesulphonate of which, formed by the action of the methanesulphonic acid in the ethanol, melts at 220° C.

N.M.R. spectrum of the product obtained:

| aromatics | δ: 7.2–8.2 ppm |
| CH$_2$N and CH$_2$CO | δ: 2.5–3.2 ppm |

EXAMPLE 11

2-[3(R)-Ethenyl-4(S)-Piperidyl]-1-(2-Phenyl-4-Quinolyl) Ethanone

The operation is as in Example 2, but starting from 39.9 g of potassium t-butylate, 30.8 g of methyl (2-phenyl-quinoline)-4-carboxylate and 35.4 g of ethyl [1- benzoyl-3(R)-ethenyl-4(S)-piperidyl]-acetate. 8 g of 2-[3(R)-ethenyl-4(S)-piperidyl]-1-(2-phenyl-4-quinolyl) ethanone are finally obtained in the form of dihydrochloride which melts at 210° C.

N.M.R. spectrum of the product obtained:

| | |
|---|---|
| COCH$_2$ | δ: 3 ppm |
| H$_{11}$, H$_{10}$ (structure) | δ H$_{10}$: 6.2 ppm |
| H$_{11'}$ (structure with NH) | δ H$_{11'}$: 5 ppm |

EXAMPLE 12

4-[2-(4-Piperidyl)-Ethyl]-Quinoline

A mixture of 13 g of 2-(4-piperidyl)-1-(4-quinolyl)-ethanone, prepared as indicated in Example 1, and 10 ml of 98% hydrazine hydrate in 150 ml of diethylene glycol is heated at 180° C. for 2 hours. After cooling, 15 g of sodium hydroxide pellets are added and the mixture is kept at 180° C. for 18 hours. The reaction mixture is diluted with water, extracted with chloroform. The organic phase is washed with water, dried and evaporated under reduced pressure. 10 g of the desired product are obtained, which is converted into the hydrochloride by the action of hydrochloric acid in ethanol. 7.2 g of 4-[2-(4-piperidyl)-ethyl]-quinoline are obtained in the form of monohydrated dihydrochloride which melts at 210° C.

N.M.R. spectrum of the product obtained:

| | |
|---|---|
| aromatics | δ: 7.2-8.6 ppm |
| N—CH$_2$ | δ: 2.6-3.1 ppm |
| Ar—CH$_2$ | δ: 3.1 ppm |

EXAMPLE 13

6-Methoxy-4-[2-(4-Piperidyl)-Ethyl]-Quinoline

The operation is an in Example 12, but starting from 43.2 g of 1-(6-methoxy-4-quinolyl)-2-(4-piperidyl)-ethanone, prepared as indicated in Example 2, 23.2 g of 98% hydrazine hydrate and 25.3 g of potassium hydroxide in 228 ml of diethylene glycol. 40.8 g of 6-methoxy-4-[2-piperidyl)-ethyl]quinoline are obtained, of which the dihydrochloride melts at 234° C.

N.M.R. spectrum of the product obtained:

| | |
|---|---|
| aromatics | δ: 7.1-8.1 ppm |
| CH$_3$O | δ: 3.9 ppm |
| CH$_2$Ar and CH$_2$N | δ: 2.2-3.2 ppm |

EXAMPLE 14

6-Methoxy-4-{2-[3(R)-Ethenyl-4(R)-Piperidyl]-Ethyl}-Quinoline

A solution of 21 g of 2-[3(R)-ethenyl-4(S)-piperidyl]-1-(6-methoxy-4-quinolyl)-ethanone, prepared as indicated in Example 3, and 20 ml of 98% hydrazine hydrate in 200 ml of diethylene glycol is heated at 180° C. for 15 minutes. The mixture is cooled to 60° C., 15 g of sodium hydroxide pellets are introduced and the mixture is heated at 180° C. for 2 hours. The reaction mixture is diluted with 500 ml of water and extracted three times with 200 ml each time of methylene chloride. The organic phase is washed with water, dried and evaporated to dryness under reduced pressure. 18 g of an oil are obtained, which is subjected to the action of hydrochloric acid in ethanol. 2.5 g of 6-methoxy-4-{2-[3(R)-ethenyl-4(R)-piperidyl]-3thyl}-quinoline in the form of the monohydrated dihydrochloride which melts at 200° C., are thus obtained.

N.M.R. spectrum of the product obtained:

| | |
|---|---|
| aromatics | δ: 7-8.6 ppm |
| Ar—CH$_2$ and CH$_2$—N | δ: 3 ppm |
| CH$_3$O | δ: 3.9 ppm |
| CH—C (H) | δ: 5 ppm |
| C (H) =CH$_2$ | δ: 6 ppm |

EXAMPLE 15

6-Methoxy-4-[2-(3-Methyl)-4-Piperidyl)-Ethyl]-Quinoline (Trans Isomer, Racemic)

The operation is as in Example 14, but starting from 3.7 g of 2-(3-methyl-4-piperidyl)-1-(6-methoxy-4-quinolyl)-ethanone (trans isomer, racemic), prepared as indicated in Example 4, 3.7 g of 98% hydrazine hydrate and 3.7 g of sodium hydroxide in 37 ml of diethylene glycol. 1.7 g are obtained of 6-methoxy-4-[2-(3-methyl-4-piperidyl)-ethyl]-quinoline (trans isomer), the acid fumarate of which prepared by the action of fumaric acid in ethanol, melts at 224° C.

N.M.R. spectrum of the product obtained:

| | |
|---|---|
| aromatics | δ: 7 to 8.6 ppm |
| Ar—CH$_2$ and CH$_2$—N | δ: 3 ppm |
| CH$_3$O | δ: 3.9 ppm |
| CH$_3$ | δ: 0.95 ppm |

EXAMPLE 16

2-Phenyl-4-[2-(4-Piperidyl)-Ethyl]-Quinoline

The operation is as in Example 14, but starting from 63.3 of 1(2-phenyl-4-quinolyl)-2-(4-piperidyl)-ethanone, prepared as indicated in Example 5, 29.3 g of 98% hydrazine hydrate and 32 g of potassium hydroxide in 300 ml of diethylene glycol. 53.6 g are obtained of 2-phenyl-4-[2-(4-piperidyl)-ethyl]-quinoline in the form of monohydrochloride melting at 219° C.

N.M.R. spectrum of the product obtained:

| | |
|---|---|
| aromatics | δ: 7.3-8.3 ppm |
| CH$_2$Ar and CH$_2$—N | δ: 2.2-3.2 ppm |

EXAMPLE 17

2-(4-Chloro-Phenyl)-4-[2-(4-Piperidyl)-Ethyl]-Quinoline

The operation is as in Example 14, but starting from 6 g of 1-[2-(4-chloro-phenyl)-4-quinolyl]-2-(4-piperidyl-)ethanone, prepared as indicated in Example 7, 2.5 g of 98% hydrazine hydrate and 2.73 g of potassium hydroxide in 25 ml of diethylene glycol. 2.1 g are obtained of 2-(4-chloro-phenyl)-4-[2-(4-piperidyl)-ethyl]-quinoline in the form of monohydrochloride, which melts above 260° C.

N.M.R. spectrum of the product obtained:

| aromatics | δ: 7.3–8.2 ppm |
| --- | --- |
| CH$_2$Ar and N—CH$_2$ | δ: 2.2–3.4 ppm |

EXAMPLE 18

2-(4-Methoxy-Phenyl)-4-[2-(4-Piperidyl)-Ethyl]-Quinoline 5.2 g of 98% hydrazine hydrate are added to 10.8 g of 1-[2-(4-methoxy-phenyl)-4-quinolyl]-2-(4-piperidyl)-ethanone prepared as indicated in Example 9, in solution in 50 ml of diethylene glycol, and the reaction medium is heated for 30 minutes at 160° C. The temperature is then reduced to 120° C. and then 5.6 g of potassium hydroxide pellets are introduced all at once. The mixture is then heated for 20 hours at 160° C., then poured into 450 ml of water. The resulting medium is then extracted with 240 ml of chloroform. The chloroform phase is washed with 250 ml of water, dried over magnesium sulphate, then concentrated. The residue is treated with a solution of hydrochloric acid in ethanol. 7.1 g of 2-(4-methoxy-phenyl)-4-[2-(4-piperidyl-ethyl]-quinoline, in the form of monohydrochoride melting above 260° C., are thus obtained:

N.M.R. spectrum of the product obtained:

| aromatics | δ: 6.8–8.2 ppm |
| --- | --- |
| CH$_2$N and CH$_2$—Ar | δ: 2.1–3.3 ppm |
| CH$_3$O | δ: 3.8 ppm |

EXAMPLE 19

2-(4-Methyl-Phenyl)-4-[2-(4-Piperidyl)-Ethyl]-Quinoline

The procedure is as in Example 18, starting from 20 g of 1-[2-(4-methyl-phenyl)-4-quinolyl]-2-(4-piperidyl)-ethanone, prepared as indicated in Example 8, 5.6 g of hydrazine hydrate and 2.4 g of sodium hydroxide in solution in 200 ml of diethylene glycol. After acidification of the residue with a solution of hydrochloric acid in ethanol, 6.2 g are obtained of 2-(4-methyl-phenyl-4-[2-(4-piperidyl)-ethyl]-quinoline in the form of monohydrochloride melting at 252° C.

N.M.R. spectrum of the product obtained:

| aromatics | δ: 7.1–8.2 ppm |
| --- | --- |
| CH$_3$—Ar | δ: 2.3 ppm |
| CH$_2$—N and CH—Ar | δ: 2.2–3.3 ppm |

EXAMPLE 20

7-Chloro-2-Phenyl-4-[2-(4-Piperidyl)-Ethyl]-Quinoline

The operation is as in Example 18, starting from 13.5 g of 1-(7-chloro-2-phenyl-4-quinolyl)-2-(4-piperidyl)-ethanone prepared as indicated in Example 10, 6 g of 98% hydrazine hydrate and 2.4 g of sodium hydroxide in 200 ml of diethylene glycol. 4.5 g of 7-chloro-2-phenyl-4-[2-(4-piperidyl)-ethyl]-quinoline are obtained, the monohydrochloride of which, formed by the action of hydrochloric acid in isopropanol, melts at 195° C.

N.M.R. spectrum of the product obtained:

| aromatics | δ: 7.2–8.2 ppm |
| --- | --- |
| CH$_2$N and CH$_2$Ar | δ: 2.2–3.2 ppm |

EXAMPLE 21

1-[2-(4-Methyl-Phenyl)-4-Quinolyl]-2-[1-(2-Phenyl-Ethyl)-4-Piperidyl]-Ethanone 3.45 g of potassium carbonate and 1.39 g of 2-phenylethyl bromide are added to a solution of 1.72 g of 1-[2-(4-methyl-phenyl)-4-quinolyl]-2-(4-piperidyl)-ethanone, prepared as indicated in Example 8, in 25 ml of dimethylformamide. The suspension, well stirred, is heated for 5 hours at 60° C., then poured into 1 liter of ice-water. The oil which separates is decanted, washed with water, then 100 ml of ether and 100 ml of a 1 N aqueous solution of hydrochloric acid are added. The precipitate formed is filtered, washed with water and then with acetone. 2 g of 1[2-(4-methyl-phenyl)-4-quinolyl]-2-[1-(2-phenyl-ethyl)-4-piperidyl]-ethanone are obtained in the form of dihydrochloride melting at 195° C.

N.M.R. spectrum of the product obtained:

| aromatics | δ: 7–8.3 ppm |
| --- | --- |
| CH$_3$Ar | δ: 2.4 ppm |
| CH$_2$N and CH$_2$CO | δ: 2.2–3.2 ppm |

EXAMPLE 22

4-{2-[1-(2-Phenyl-Ethyl)-4-Piperidyl]-Ethyl}-2-Phenyl-Quinoline

The operation is as in Example 21, starting from 9.3 g of the monohydrochloride of 2-phenyl-4-[2-(4-piperidyl)-ethyl]-quinoline, prepared as indicated in Example 16, 7.3 g of 2-phenyl-ethyl bromide and 18.1 g of potassium carbonate, in suspension in 130 ml of dimethylformamide. 8.3 g are obtained of 4-{2-[1-(2-phenyl-ethyl)-4-piperidyl]-ethyl}-2-phenyl-quinoline melting at 80° C.

N.M.R. spectrum of the product obtained:

| aromatics | δ: 7.1–8.2 ppm |
| --- | --- |
| CH$_2$N and CH$_2$Ar | δ: 2.4–3.8 ppm |
| C$_6$H$_5$ | δ: 7.2 ppm |

EXAMPLE 23

4-[2-(1-Methyl-4-Piperidyl)-Ethyl]-2-Phenyl-Quinoline 5 g of lithium aluminum hydride was progressively introduced, incrementally, in 200 ml of dry tetrahydrofuran, under an atmosphere of nitrogen. The suspension obtained is cooled to 0° C., then a solution of 20 g of 4-[2-(1-ethoxycarbonyl-4-piperidyl)-ethyl]-2-phenyl quinoline in 200 ml of tetrahydrofuran is added drop by drop, the temperature of the reaction mixture being maintained below 30° C. After 4 hours of contact at the ambient temperature, there are introduced very slowly and successively 5.85 ml of water, 4.3 ml of a 5 N aqueous solution of sodium hydroxide, then 19.5 ml of water. The mineral products are separated by filtration and washed twice with 30 ml of methylene chloride each time. The filtrates are collected, dried over magnesium sulphate, then evaporated to dryness. The residue obtained, which is constituted by the desired product, is acidified with the equivalent quantity of a solution of hydrochloric acid in ethanol. 11.1 g of 4-[2-(1-methyl-4-piperidyl)-ethyl]-2-phenyl quinoline in the form of monohydrochloride melting at 206° C. are obtained.

N.M.R. spectrum of the product obtained:

| aromatics | δ: 7.3–8.6 ppm |
|---|---|
| $CH_2N$ and $CH_2Ar$ | δ: 2.6–3.6 ppm |
| $CH_3N$ | δ: 2.7 ppm |

The 4-[2-(1-ethoxycarbonyl-4-piperidyl)-ethyl]-2-phenyl-quinoline is prepared as follows:

A solution of 15.6 g of 2-phenyl-4-[2-(4-piperidyl)ethyl] quinoline, prepared as indicated in Example 16, in 200 ml of chloroform is treated with stirring with 200 ml of a 1 N aqueous solution of sodium hydroxide. Then 21.7 g of ethyl chloroformate are added, drop by drop, and the suspension obtained is stirred for 17 hours at the ambient temperature. After separation, the organic phase is washed with water, dried over magnesium sulphate, then evaporated under reduced pressure. 20 g of 4-[2-(1-ethoxycarbonyl-4-piperidyl)-ethyl]-2-phenyl-quinoline in the form of an oil are obtained.

N.M.R. spectrum of the product obtained:

| aromatics | δ: 6.8–8.2 ppm |
|---|---|
| $CH_2-N-\underset{\underset{O}{\|}}{C}-$ | δ: 3.8–4.2 ppm |

EXAMPLE 24

4-[2-(4-Piperidyl)-Ethyl]-Quinoline

A solution of 11.4 g of 3-[2-(4-piperidyl)-ethyl]indole in 200 ml of methylene chloride is cooled to −30° C., then 80 ml of a 1.6 M solution of methyllithium in ether are added, drop by drop, under an atmosphere of nitrogen. The reaction mixture is then left at the ambient temperature for 15 hours. The excess of methyllithium is destroyed by addition of 20 ml of ethanol, then 200 ml of distilled water are added. The organic phase is separated by decantation, washed with 200 ml of water, dried over magnesium sulphate and evaporated. 10 g of a mixture containing principally the 4-[2-(4-piperidyl)-ethyl]-quinoline are obtained.

This mixture is fixed on a silica column, then it is eluted with an eluant consisting of a (90/10) chloroformdiethylamine mixture. 3.1 g of 4-[2-(4-piperidyl)-ethyl]-quinoline, the hydrochloride of which melts at 230° C. are thus obtained.

N.M.R. spectrum of the product obtained:

| aromatics | δ: 6.8–8.2 ppm |
|---|---|
| $CH_2N$ and $CH_2Ar$ | δ: 2.1–3.3 ppm |

The 3-[2-(4-piperidyl)-ethyl]indole can be prepared as indicated in the French Pat. No. 2,334,358.

EXAMPLE 25

6-Methoxy-2-Phenyl-4-[2-(4-Piperidyl)-Ethyl]-Quinoline

A solution of 5 g of 6-methoxy-4-[2-(1-benzoyl-4-piperidyl)-ethyl] quinoline-N-oxide in 240 ml of dry tetrahydrofuran is added, drop by drop, to 75 ml of a 1.9 M solution of phenyl lithium in a mixture of 70% of benzene and 30% of ether, stirred under an atmosphere of nitrogen and cooled to 0° C. The reaction mixture is then stirred for 4 hours at the ambient temperature, then poured into a mixture of 300 ml of ice-water and 150 ml of a 2 N aqueous solution of hydrochloric acid.

The aqueous phase, separated by decantation, is washed twice with 100 ml of chloroform each time, then made alkaline by 150 ml of a 2 N aqueous solution of sodium hydroxide.

The oily suspension obtained in extracted twice with 100 ml of chloroform. The organic phases are collected, washed with 100 ml of water, dried over magnesium sulphate, then concentrated by elimination of the chloroform. 4.6 g of an oil are obtained, which is dissolved in 100 ml of a 5 N aqueous solution of hydrochloric acid. The solution obtained is heated under reflux for 15 hours, then extracted twice with 50 ml each time of ether. The residual aqueous solution is made alkaline by means of an 11 N aqueous solution of sodium hydroxide and then extracted twice with 50 ml of methylene chloride each time. The extract, dried over magnesium sulfate, is concentrated by elimination of the methylene chloride and the residue is fixed on a column of silica. It is then eluted with a 90/10 mixture of chloroform and diethylamine.

1.5 g are thus obtained of 6-methoxy-2-phenyl-4-[2-(4-piperidyl)-ethyl]-quinoline, the monohydrochloride of which melts at 210° C.

N.M.R. spectrum of the product obtained:

| aromatics | δ: 7.2–8.2 ppm (m) |
|---|---|
| $CH_3O$ | δ: 3.9 ppm (s) |
| $CH_2Ar$ and $CH_2N$ | δ: 2.2–3.3 ppm (m) |

The 6-methoxy-4-[2-(1-benzoyl-4-piperidyl)ethyl]-quinoline N-oxide, the starting product, is prepared in the following way:

269 ml of a 0.09 M solution of monoperphthalic acid in ether (prepared according VOGEL-Textbook of Practical Organic Chemistry, 1978,307) are added rapidly to a solution of 7.9 g of 6-methoxy-4-[2-(1-benzoyl-4-piperidyl)-ethyl]-quinoline in 45 ml of methanol, stirred and cooled to 10° C. After four hours at the ambient temperature, a further 20 ml of the same monoperphthalic acid solution are added, and the stirring is then maintained for 15 hours. The reaction mixture is then made alkaline with 100 ml of a 0.7 N aqueous solution of sodium hydroxide. The organic phase, separated, is again washed with 100 ml of a 0.5 N solution of sodium hydroxide, dried, then concentrated. The residue obtained, after recrystallization from cyclohexane, gives 5.1 g of 6-methoxy-4-[2-(1-benzoyl-4-piperidyl)-ethyl]quinoline-N-oxide melting at 138° C.

N.M.R. spectrum of the product obtained:

| | |
|---|---|
| $H_2$ | δ: 9.2 ppm |
| $H_1$ | δ: 9.4 ppm |
| $CH_3-O-$ | δ: 4 ppm |

The 6-methoxy-4-[2-(1-benzoyl-4-piperidyl)-ethyl]-quinoline is prepared in the following way:

18.2 g of triethylamine are added, in period of half an hour, to a stirred suspension of 20.7 g of 6-methoxy-4-[2-(4-piperidyl)-ethyl]-quinoline dihydrochloride, prepared as indicated in Example 13, in 150 ml of 1,1,1-trichloro-ethane. The mixture is cooled in an ice bath and there are introduced, in half an hour, 8.5 g of benzoyl chloride. The mixture is then stirred at ambient temperature for 15 hours. The reaction is poured into 1500 ml of water and the organic phase, separated by decantation, is washed successively with 500 ml of a 1 N aqueous solution of sodium hydroxide, 100 ml of water, 100 ml of a 5% aqueous solution of acetic acid, then 3 times with 100 ml of water, each time. The organic phase is then dried over magnesium sulphate, then concentrated by elimination of the solvent.

15.7 g of 4[2-(1-benzoyl-4-piperidyl)-ethyl]-6-methoxyquinoline in the form of a oil are thus obtained.

N.M.R. spectrum of the product obtained:

| aromatics | δ: 6.8–8.2 ppm |
| CH₃O | δ: 3.9 ppm |
| CH₂—N—CO | δ: 4 ppm |

EXAMPLE 26

6-Methoxy-4-{2-[3(S)-Ethenyl-4(R)-Piperidyl]-Ethyl}-Quinoline 5 g of 6-methoxy-4-{2-[3(R)-ethenyl-4(R)-piperidyl]-ethyl}-quinoline, prepared as indicated in Example 14, are dissolved in 400 ml of water and the pH is brought to 6 by addition of a 2 N aqueous solution of hydrochloric acid.

The solution obtained is heated at 160° C, in an autoclave for 24 hours, then it is made alkaline by addition of sodium carbonate and extracted four times with 150 ml methylene chloride each time. The organic phase is washed with water, dried over sodium sulphate and evaporated under reduced pressure. 5 g of an oil are thus obtained which is treated with a solution of hydrochloric acid in ethanol.

In this way 1.6 g are obtained of 6-methoxy-4-{2-[3(S)-ethenyl-4(R)-piperidyl]-ethyl}-quinoline, in the form of monohydrated dihydrochloride melting at 206° C.

N.M.R. spectrum of the product obtained:

| aromatics | δ: 7.1–8.6 ppm |
| CH₃O | δ: 3.9 ppm |
| C(H)=CH₂ | δ: 5.4 ppm |
| CH=C(H) | δ: 5 ppm |
| Ar—CH₂— | δ: 3 ppm |

EXAMPLE 27

1-(6-Methyl-2-Phenyl-4-Quinolyl)-2-(4-Piperidyl)-Ethanone

The operation is as in Example 6, starting from 17.6 g of sodium hydride (50% suspension in vaseline oil), 22.3 g of methyl (6-methyl-2-phenyl-quinoline)-4-carboxylate and 21 g of methyl (1-benzoyl-4-piperidyl)acetate. 24.5 g of 1-(6-methyl-2-phenyl-4-quinolyl)-B 2-(4-piperidyl)-ethanone are finally obtained, the hydrochloride of which melts above 260° C.

N.M.R. spectrum of the product obtained:

| aromatics | δ: 7.2–8.1 ppm |
| CH₂N and CH₂CO | δ: 2.4–3.1 ppm |
| CH₃Ar | δ: 2.4 ppm |

EXAMPLE 28

6-Methyl-2-Phenyl-4-[2-(4-Piperidyl)-Ethyl]-Quinoline

The operation is as indicated in Example 18, except that the heating is for 4 hours at 160° C. instead of the 20 hours and that one starts with the amount of 1-(6-methyl-2-phenyl-4-quinolyl)-2-(4-piperidyl)-ethanone equivalent to 12.6 g of the corresponding hydrochloride, 6.2 g of 80% hydrazine hydrate and 5.6 g of sodium hydroxide in pellets in 50 ml of diethylene glycol.

After recrystallization from ethanol, 7.1 g are obtained of 6-methyl-2-phenyl-4-[2-(4-piperidyl)-ethyl]-quinoline in the form of the monohydrochloride melting at 223° C.

N.M.R. spectrum of the product obtained.

| aromatics | δ: 7.1–8.2 ppm |
| CH₂N and CH₂Ar | δ: 2.3–3.3 ppm |

EXAMPLE 29

1-[2-(2-Chloro-Phenyl)-4-Quinolyl]-2-(4-piperidyl)-Ethanone

The operation is as in Example 6, starting from 27 g of sodium hydride (50% suspension in vaseline oil), 36.7 g of methyl [2-(2-chloro-phenyl)-quinoline]-4-carboxylate and 32.1 g of methyl (1-benzoyl-4-piperidyl)-acetate. 39.2 g of 1-[2-(2-chloro-phenyl)-4-quinolyl]-2-(4-piperidyl)-ethanone are finally obtained, the hydrochloride of which melts at 246° C.

N.M.R. spectrum of the product obtained:

| aromatics | δ: 7.1–8.4 ppm |
| CH₂N and CH₂CO | δ: 2.3–3.1 ppm |

EXAMPLE 30

2-(2-Chloro-Phenyl)-4-[2-(4-Piperidyl)-Ethyl]-Quinoline

The operation is as in Example 28, starting from the amount of 1-[2-(2-chloro-phenyl)-4-quinolyl]-2-(4-piperidyl)-ethanone equivalent to 17.1 g of the corresponding hydrochloride, 8 g of 80% hydrazine hydrate and 7.1 g of potassium hydroxide pellets in 65 ml of diethyleneglycol. 9 g are obtained of 2-(2-chlorophenyl)-4-[2-(4-piperidyl)-ethyl]-quinoline, of which the fumarate melts at 210° C.

N.M.R. spectrum of the product obtained:

| aromatics | δ: 7.1–8.2 ppm |
| CH₂N and CH₂Ar | δ: 2.2–3.2 ppm |

PHARMACOLOGICAL PROPERTIES

I-AFFINITY FOR THE CEREBRAL RECEIVING SITES OF THE BENZODIAZEPINES

This affinity is measured by the capacity of the products for displacing the tritiated Diazepam ($^3$H Diazepam) from its binding site and is expressed by a value $K_i$, in micromoles ($\mu$M), which is calculated by the formula:

$$K_i = \frac{IC_{50}}{1 + \frac{C}{K_D}}$$

in which C represents the concentration of $^3$H Diazepam, $K_D$ is a constant of affinity equal to 2.74 mM and $IC_{50}$ is the concentration necessary to obtain an inhibition of 50% of the binding of the $^3$H Diazepam.

The products have been tested according to the method of MOHLER et al, Life Science, 1977, 20, 2101, which is relied on herein. The following results have been obtained:

| Products | $K_i$ ($\mu$M) | Products | $K_i$ ($\mu$M) |
|---|---|---|---|
| Example 6 | 8 | Example 13 | 7 |
| Example 7 | 4.5 | Example 23 | 0.1 |
| Example 5 | 0.5 | Example 25 | 11 |
| Example 11 | 2 | Example 24 | 13 |
| Example 9 | 5 | Example 3 | 16 |
| Example 8 | 1.6 | Example 14 | 5 |
| Example 18 | 1.3 | Example 22 | 0.5 |
| Example 17 | 0.4 | | |
| Example 16 | 0.2 | | |
| Example 19 | 0.6 | | |

II-ANTIARHYTHMIC ACITIVTY

The antiarhythmic activity of the compounds of the present invention has been shown with the help of the aconitine test on the rat.

The principle of the technique rests on the induction time of the ventricular arhythmia caused by aconitine which slowly perfused in rats. An antiarhythmic substance retards the appearance of the arhythmia and the delay is proportional to the activity of the molecule.

Groups of 5 male rats are used. An individual anaesthesia is carried out (10% urethane; 1 g/kg/ip) to permit a catheterisation of the vein of the penis. The electrocardiogram is recorded. At the time T=0 the substance studied is injected in the form of an aqueous solution, at the rate of 2.5 ml of solution per kg in 30 seconds. At the time T=90 seconds, that is 1 minute after the end of the injection, the aconitine is perfused at the rate of 20 $\mu$g per minute until the appearance of supraventricular extra systoles. The time of perfusion of the aconitine is noted.

The results are expressed by an $ED_{50}$ which is the dose in mg/kg increasing by 50% the time of perfusion of the aconitine in comparison with the perfusion time of aconitine for the control animals.

The results obtained are collected in the following table:

| Products | $ED_{50}$ mg/kg (i.v.) |
|---|---|
| Example 16 | 1.3 |
| Example 14 | 5 |
| Example 26 | 2.6 |

TOXICOLOGICAL PROPERTIES

The acute toxicities of the compounds according to the invention have been determined on the male mouse $CD_1$ (Charles River) by the oral method. The $LD_{50}$ have been calculated, after 3 days observation, by the cumulative method of J. J. REED and H. MUENCH. (Amer. J. Hyg. 1938, 27, 493).

The compounds behave like substances of relatively low toxicity to mice, since the $LD_{50}$ of the compounds are between 200 and 1000 mg/kg.

THERAPEUTIC USE

The compounds of the invention and their pharmaceutically acceptable salts can be used in human therapeutics, in the form of tablets, capsules, gelatin-coated pills, suppositories, ingestable or injectable solutions, with a solid or liquid pharmaceutically acceptable non-toxic carrier, etc., as antiarhythmics, hypnotics, anticonvulsivants and for the treatment of states of anxiety and of various psychoneurotic states. Such pharmaceutical carriers can be sterile liquids, such as water and oils, including those of petroleum, animal, vegetable or synthetic origin, such as peanut oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatine, malt, rice, flour, chalf, silica gel, magnesium carbonate, magnesium stearate, sodium stearate, glycerol monostearate, talc, sodium chloride, dried skim milk, glycerol, propylene glycol, water, ethanol and the like. These compositions can take the form of solutions, suspensions, tablets, pills, capsules, powders, sustained-release formulations and the like. Suitable pharmaceutical carriers are described in "Remington's Pharmaceutical Sciences" by E. W. Martin. Such compositions will contain an effective therapeutic amount of the active compound together with a suitable amount of carrier so as to provide the form for proper administration to the host. While intravenous injection is a very effective form of administration, other modes can be employed.

The posology depends on the desired effects and the method of administration used. For example, taken orally, it can be between 5 and 250 mg of active substance per day, with unitary does ranging from 1 to 50 mg. The posology per day refers to total weight of the patient. Dosage per day expressed in milligrams per unit of weight of human is 0.1 mg per kg to 5 mg per kg.

We claim:

1. A compound of the formula:

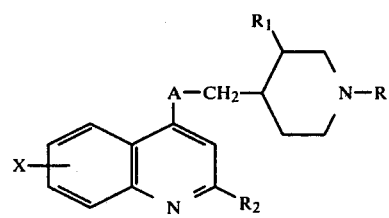

in which
R is hydrogen, alkyl having 1 to 4 carbons or phenylalkyl of which the alkyl has one or two carbons, $R_1$ is hydrogen, alkyl having 1 to 4 carbons or alkenyl of 2 to 4 carbons, $R_2$ is phenyl or phenyl substituted by one substituent taken from the halogens, alkyl and alkoxy having 1 to 4 carbons X is fixed in position 5, 6, 7 or 8 on the quinoline ring and represents hydrogen, halogen, or alkyl having 1 to 4 carbons and A represents CO or $CH_2$, and its addition salts with pharmaceutically acceptable acids.

2. The compound according to claim 1 in which X represents hydrogen and A represents $CH_2$, and its addition salts with pharmaceutically acceptable acids.

3. The compound according to claim 2 of the formula:

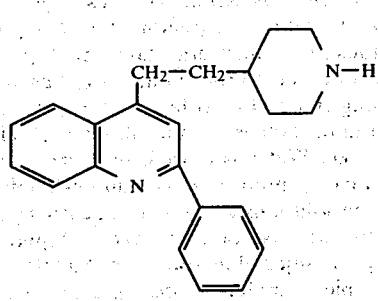

and its addition salts with pharmaceutically acceptable acids.

4. The compound according to claim 1 in which $R_1$ is hydrogen.

5. The compound according to claim 1 in which $R_1$ is alkyl having 1 to 4 carbons or alkenyl of 2 to 4 carbons, and said compound is a racemic or enantiomeric diastereoisomer compound.

6. The compound according to claim 1 which is 1-(2-phenyl-4-quinolyl)-2-(4-piperidyl)-ethanone, and its addition salts with pharmaceutically acceptable acids.

7. The compound according to claim 1 which is 1-[2-(4-methyl-phenyl)-4-quinolyl]-2-(4-piperidyl)-ethanone, and its addition salts with pharmaceutically acceptable acids.

8. The compound according to claim 1 which is 2-[3(R)-ethenyl-4-(S)-piperidyl]-1-(2-phenyl-4-quinolyl)-ethanone and its addition salts with pharmaceutically acceptable acids.

9. The compound according to claim 1 which is 2-(4-chloro-phenyl)-4-[2-(4-piperidyl)-ethyl]-quinoline, and its addition salts with pharmaceutically acceptable acids.

10. The compound according to claim 1 which is 2-(4-methoxy-phenyl)-4-[2-(4-piperidyl)-ethyl]-quinoline, and its addition salts with pharmaceutically acceptable acids.

11. The compound according to claim 1 which is 2-(4-methyl-phenyl)-4-[2-(4-piperidyl)-ethyl]-quinoline, and its addition salts with pharmaceutically acceptable acids.

12. The compound according to claim 1 which is 4-{2-[1-(2-phenyl-ethyl)-4-piperidyl]-ethyl}-2-phenyl-quinoline, and its addition salts with pharmaceutically acceptable acids.

13. The compound according to claim 1 which is 4-[2-(1-methyl-4-piperidyl)-ethyl]-2-phenyl-quinoline, and its addition salts with pharmaceutically acceptable acids.

14. The compound according to claim 1 which is 2-(2-chloro-phenyl)-4-[2-(4-piperidyl)-ethyl]-quinoline, and its addition salts with pharmaceutically acceptable acids.

* * * * *